United States Patent
Liu et al.

(10) Patent No.: US 10,247,747 B2
(45) Date of Patent: Apr. 2, 2019

(54) TITRATION MODULE OF BIOCHIP AND TIRATION TEST APPARATUS THEREOF

(71) Applicant: King Yuan Electronics Co., Ltd., Hsinchu (TW)

(72) Inventors: Kuang-Hsiang Liu, Hsinchu (TW); Chieh-Wen Lu, Hsinchu (TW); His-Hua Chou, Hsinchu (TW); Shih-Chan Chine, Hsinchu (TW)

(73) Assignee: King Yuan Electronics Co., Ltd., Hsinchu (TW)

( * ) Notice: Subject to any disclaimer, the term of this patent is extended or adjusted under 35 U.S.C. 154(b) by 158 days.

(21) Appl. No.: 15/424,918

(22) Filed: Feb. 6, 2017

(65) Prior Publication Data
US 2018/0106822 A1    Apr. 19, 2018

(30) Foreign Application Priority Data
Oct. 19, 2016  (TW) .............................. 105133655 A

(51) Int. Cl.
*G01N 35/10* (2006.01)
*B01L 3/02* (2006.01)

(52) U.S. Cl.
CPC ........ *G01N 35/1065* (2013.01); *B01L 3/0293* (2013.01); *G01N 35/109* (2013.01); *G01N 35/1011* (2013.01); *B01L 2300/0645* (2013.01); *B01L 2300/0819* (2013.01); *G01N 2035/1039* (2013.01)

(58) Field of Classification Search
CPC .......... G01N 35/1065; G01N 35/1011; G01N 35/1002; G01N 35/109
See application file for complete search history.

(56) References Cited

U.S. PATENT DOCUMENTS

| | | | |
|---|---|---|---|
| 5,443,792 A * | 8/1995 | Buhler ................. | G01N 35/109 422/106 |
| 6,551,849 B1 * | 4/2003 | Kenney ................. | B01L 3/0244 438/34 |
| 6,814,936 B1 * | 11/2004 | Enhorning ............ | B01L 3/0275 422/504 |
| 2006/0189890 A1 * | 8/2006 | Gooley .............. | G01N 35/1016 600/562 |
| 2014/0239986 A1 * | 8/2014 | Liu .................... | G01R 1/07307 324/750.01 |

* cited by examiner

*Primary Examiner* — Matthew D Krcha
(74) *Attorney, Agent, or Firm* — Bacon & Thomas, PLLC

(57) ABSTRACT

A titration module of biochip includes a base, a plurality of titration units, a plurality of pipelines, a transfer unit, and a control unit. The plural titration units and the plural pipelines are arranged above the base, and that the titration units each is provided, at its lower end, a needle element and a reservoir which are communicated with each other. The transfer unit is arranged on the base, and includes at least one driving device for driving, selectively, the plural titration units and the plural pipelines in a lateral direction (leftward and rightward), a longitudinal direction (frontward and rearward) and a vertical direction (upward and downward), respectively. The control unit is electrically connected with the transfer unit, and controls the same for switching, selectively, the plural titration units and the plural pipelines.

11 Claims, 12 Drawing Sheets

TITRATION MODULE OF BIOCHIP AND TIRATION TEST APPARATUS THEREOF

BACKGROUND OF THE INVENTION

Field of the Invention

The present invention relates to a titration module of biochip and titration test apparatus thereof, and more particularly, to a titration module of biochip and titration test apparatus thereof adapted for detections performed under an environment of test fluids.

Description of Related Art

Conventionally, a biochip relates to a chip structure carrying a biosensor, where such biosensor resides in a combined transducer using immobilized biomolecules; and relates to a device for detecting environmental chemicals, in vivo or in vitro, or for detecting a response resulted from a specific interaction therewith. The biosensor has a very wide scope of application, including, among others, inspecting urea by applying the theory of ion-sensitive field effect; or performing bioassays on allergen, enzyme, microorganism, cells, and so forth; or proceeding with a monitoring and analysis on environmental factors such as soil pH or ocean pH.

The biosensor, given above, mainly relates to a semiconductor-based ion sensor using an ion sensitive field effect transistor (ISFET), in the application of a theory of metal-oxide-semiconductor field-effect transistor (MOSFET), such that metal of the gate thereof is removed and replaced by using an insulative sensing diaphragm to contact directly with test fluids. An electrolysis is then carried out to the test fluids through electrodes, so that ions-to-be-tested will adsorb the insulative sensing diaphragm and an adsorption reaction will be resulted to cause a charnel. As such, a test has to be performed under an environment that the biosensor maintains in contact with the test fluids in order to achieve the purpose. Conventionally, as disclosed in documents, there have been several measures in loading test fluids, such as the one disclosed in U.S. Patent Publication No. 2014/0239986, in which a fluid well is arranged, directly, in a probe card, such that in case a biosensor is in contact with the probe card, a tightly-closed channel will be formed for transporting test fluids into a test area in the biosensor. However, such measure cannot be applied to all types of probe cards, but specifically-made fluid wells are required to carry out insulation and loading for the test fluids, making it lack of compatibility of components, let alone it is impossible to perform a replacement of different test fluids, recycle of waste fluids, and electrode electrolysis. Therefore, a significant room exists for improvement in use.

Given the above, in an attempt to solve the problem, as mentioned above, research and experiments for a "Titration Module of Biochip and Titration Test Apparatus Thereof" have been undertaken, eventually resulting in accomplishment of the present invention.

SUMMARY OF THE INVENTION

An object of the present invention is to provide a titration test apparatus of biochip, featured in utilizing a titration module of biochip to combine with a test head and a prober for integrating the same into an automatic titration test apparatus in an effective way such that test results can be transmitted instantly.

Another object of the present invention is to provide a titration module of biochip, featured in utilizing multiple titration units and pipelines with various switching actions so as to drop various test fluids into a biochip such that test speed can be increased effectively.

To achieve the above-mentioned object, the titration module of biochip comprises a base, a plurality of titration units, a plurality of pipelines, a transfer unit, and a control unit. The plural titration units and the plural pipelines are arranged above the base, that the plural pipelines are in connection with the plural titration units, and that the titration units each includes a needle element and a reservoir which are communicated with each other. The transfer unit is arranged on the base, and is connected with the plural titration units and the plural pipelines. The transfer unit includes at least one driving device for driving, selectively, the plural titration units and the plural pipelines in a lateral direction (leftward and rightward), a longitudinal direction (frontward and rearward) and a vertical direction (upward and downward), respectively. The control unit is electrically connected with the transfer unit, and controls the same for switching, selectively, the plural titration units and the plural pipelines. As such, by using the transfer unit to switch the plural titration units and the plural pipelines selectively, various test fluids can be dropped into the biochip so as to increase the speed of test effectively.

According to the present invention, at least one of the plural pipelines relates to a titration pipeline for connecting with each titration unit such that the titration pipeline can receive test fluids.

Besides, according to the present invention, the titration module may further comprise an electrode unit disposed above the base, and that the at least one driving device can drive the electrode unit in a lateral direction (leftward and rightward), a longitudinal direction (frontward and rearward) and a vertical direction (upward and downward), respectively. The electrode unit can provide power supply for dissociating ions from test fluids so as to perform bioassays.

According to the present invention, one of the plural pipelines may reside in a vacuum unit for connecting with a vacuum device. Thereby, when completion of a test, the vacuum device can remove the test fluids speedily, and that the leftover test fluid can be reduced such that test efficiency and yield rate can be increased significantly.

Further, according to the present invention, one of the plural pipelines may relate to an intake unit which is connected with an air supply device. Thereby, a biochip, following removal of the test fluids when the inspection is finished, will be proceeded with an air-blow work. By way of the air blow with compressed air, the leftover test fluid can be blown away and dried instantly. This will prevent the test fluids from flowing to electrode plates of the biochip causing a short circuit or a circuit break.

Still further, according to the present invention, each titration unit is provided, at its lower end, with a liquid reservoir and a flared flange. Thereby, in addition to keeping a sufficient test fluid inside the liquid reservoir, through the help of the arrangement of the flared flange, a "leakage distance" for flowing outward the test fluid is lengthened. This will solve the problem that the test fluid might flow to an ambient circuit board or electrode.

According to the present invention, the titration pipelines are each provided with a quantitative fluid control device for controlling titration amount of the test fluids.

Further, according to the present invention, each titration unit is provided with a micro needle array, constituted by a plurality of micro needles in a matrix arrangement, such that the test fluid can be dropped uniformly into a test area of the biochip.

Still further, each titration pipeline is provided with an electrode, and that an electrode needle element is located at an end of the reservoir for the supply of electric power. The electrode needle element may not be connected with the reservoir, and that the electrode needle element and a needle element fall into respective components. Alternatively, the electrode can be connected with the needle element through a wire, so that the needle element can supply electric power for titration. Namely, the electrode needle element and the needle element can be integrated into a single component.

According to the present invention, the titration test apparatus of biochip comprises a needle test device, a titration module, and a test head. The needle test device includes a mobile stage for carrying a biochip, and that the needle test device is fixedly arranged with a probe card above the biochip. The titration module includes a base, a plurality of titration units, a plurality of pipelines, a transfer unit, and a control unit. The plural titration units and the plural pipelines are arranged above the probe card, that the plural pipelines are in connection with the plural titration units, and that the titration units each includes a needle element and a reservoir which are communicated with each other. The transfer unit is arranged on the base, and is connected with the plural titration units and the plural pipelines. The transfer unit includes at least one driving device for driving, selectively, the plural titration units and the plural pipelines in a lateral direction (leftward and rightward), a longitudinal direction (frontward and rearward) and a vertical direction (upward and downward), respectively. The control unit is electrically connected with the transfer unit, and controls the same for switching, selectively, the plural titration units and the plural pipelines. The test head is provided with a test circuit board which is electrically connected with the probe card. This will integrate effectively into an automatic titration test apparatus such that test results can be transmitted instantly, and will increase the speed of test effectively.

Further, according to the present invention, the titration test apparatus of biochip may further comprise a monitor lens arranged on the base of titration module, where the monitor lens can monitor and align with relative positions for each of the titration units, of the pipelines, and of the biochip so as to ensure an accurate alignment.

Still further, according to the present invention, the titration test apparatus of biochip may further comprise a laser rangefinder arranged on the base of titration module, where the laser rangefinder can monitor and align with relative distances for each of the titration units, of the pipelines, and of the biochip so as to ensure an accurate alignment.

According to the present invention, a signal line is provided between the probe card and the test circuit board of the test head so as to transmit test results in real time.

Other objects, advantages, and novel features of the invention will become more apparent from the following detailed description when taken in conjunction with the accompanying drawings.

DETAILED DESCRIPTION OF THE PREFERRED EMBODIMENTS

Figure 1:
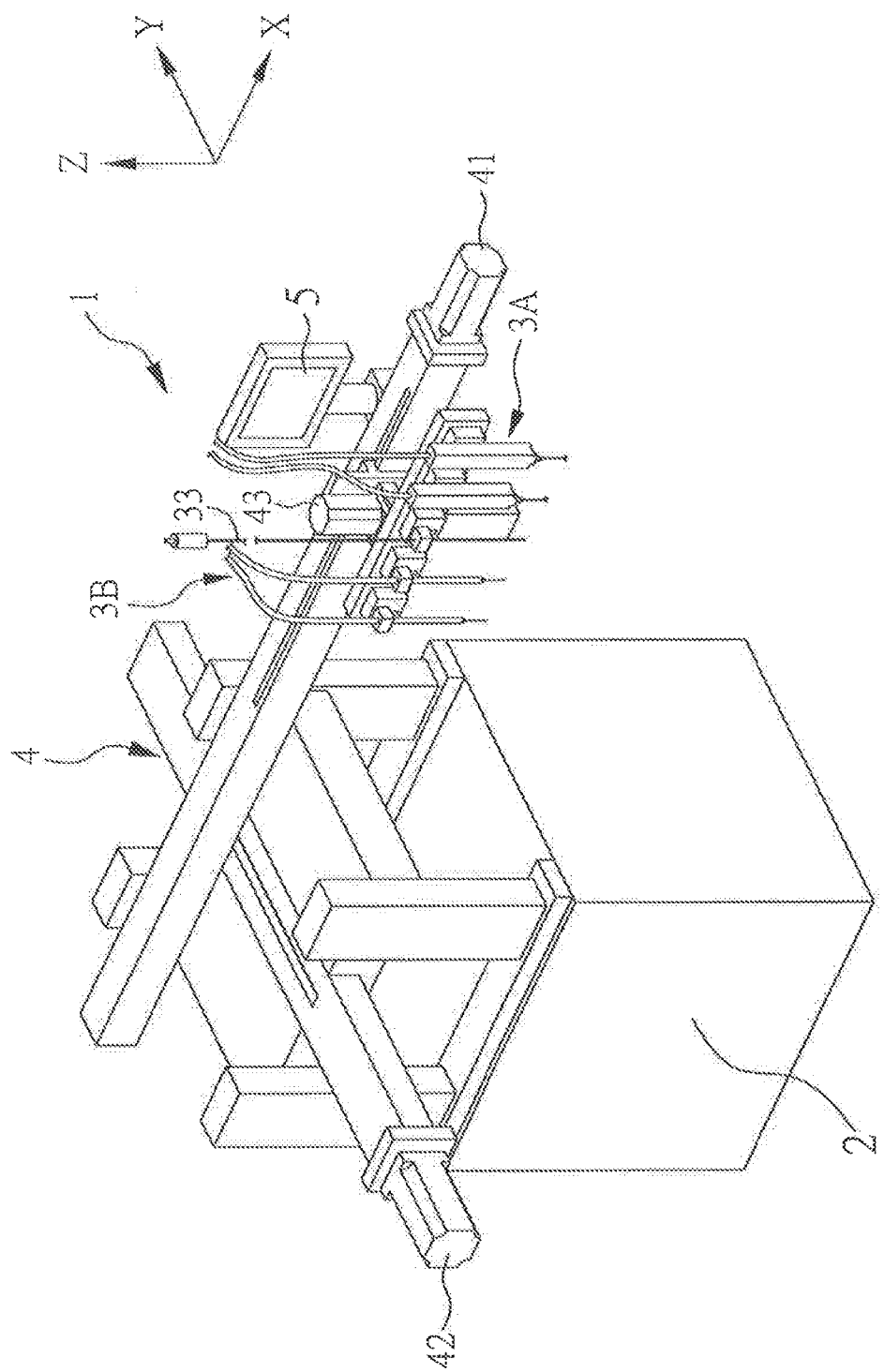
FIG. 1 is a perspective view illustration a titration module of biochip according to a first embodiment of the present invention.

Referring to FIG. 1, a perspective view illustration a titration module of biochip according to a first embodiment of the present invention, the titration module 1 of biochip comprises a base 2, a plurality of titration units 3A, an electrode unit 33, a plurality of pipelines 3B, a transfer unit 4, and a control unit 5. The plural titration units 3A, the electrode unit 33, and the plural pipelines 3B are arranged above the base 2, that the plural pipelines 3B are in connection with the plural titration units 3A, and that the transfer unit 4 is in connection with the plural titration units 3A, the plural pipelines 3B, and the electrode unit 33.

Figure 2:
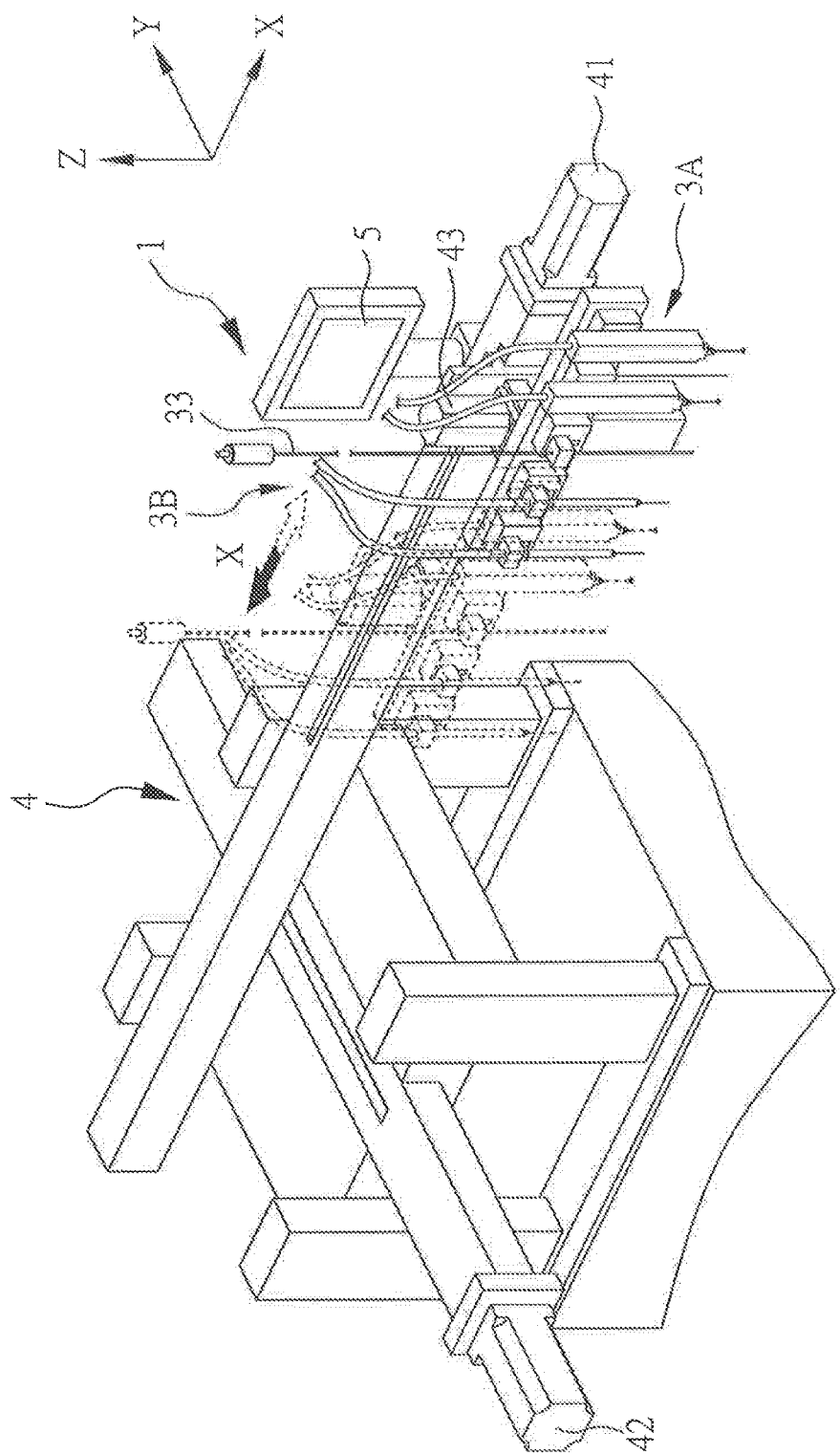
FIG. 2 is a schematic view illustrating titration units, an electrode unit, and pipelines of biochip moving alone an X-axis according to the first embodiment of the present invention.
Figure 3:
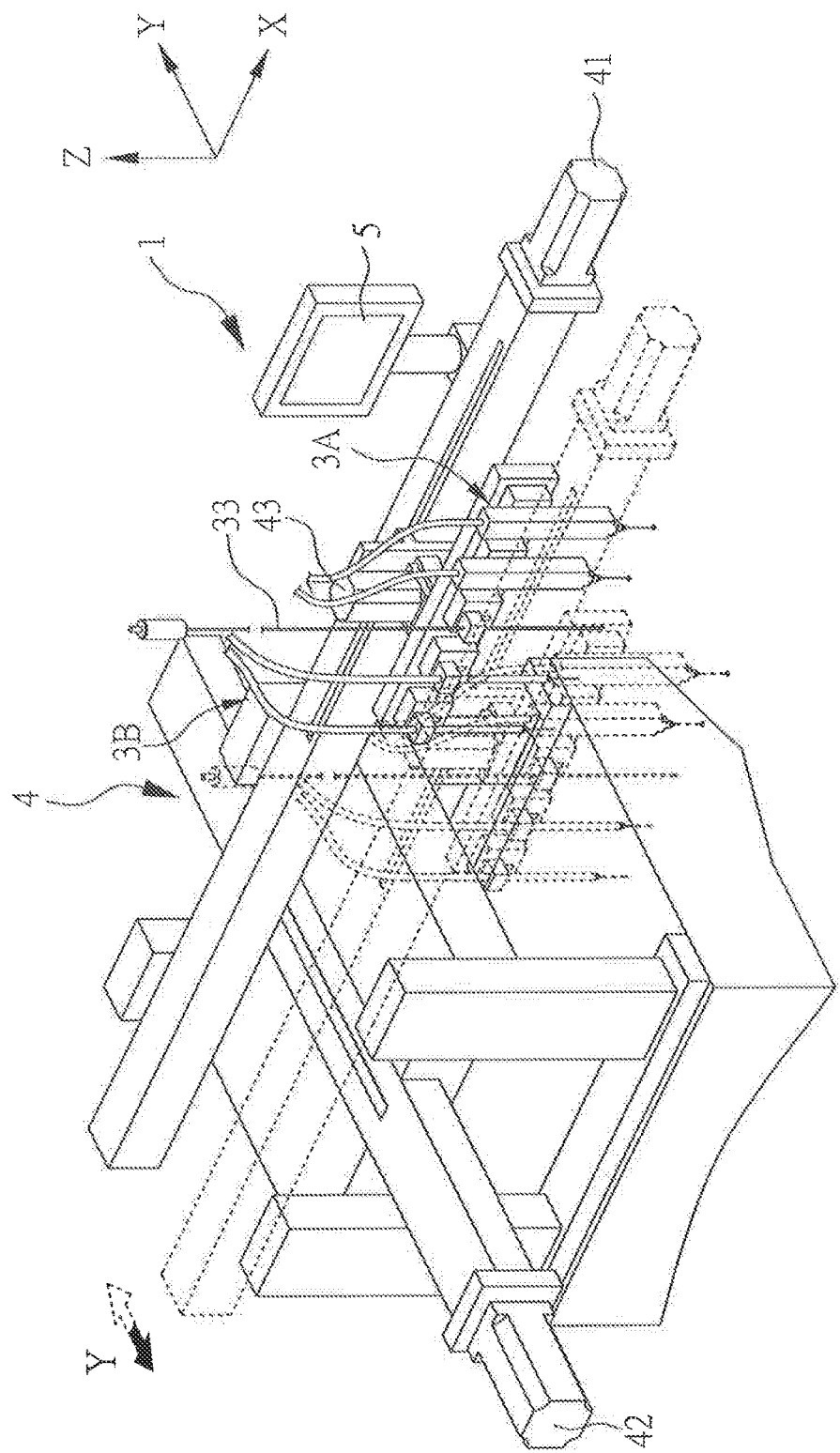
FIG. 3 is a schematic view illustrating the titration units, the electrode unit, and the pipelines of biochip moving alone a Y-axis according to the first embodiment of the present invention.
Figure 4:
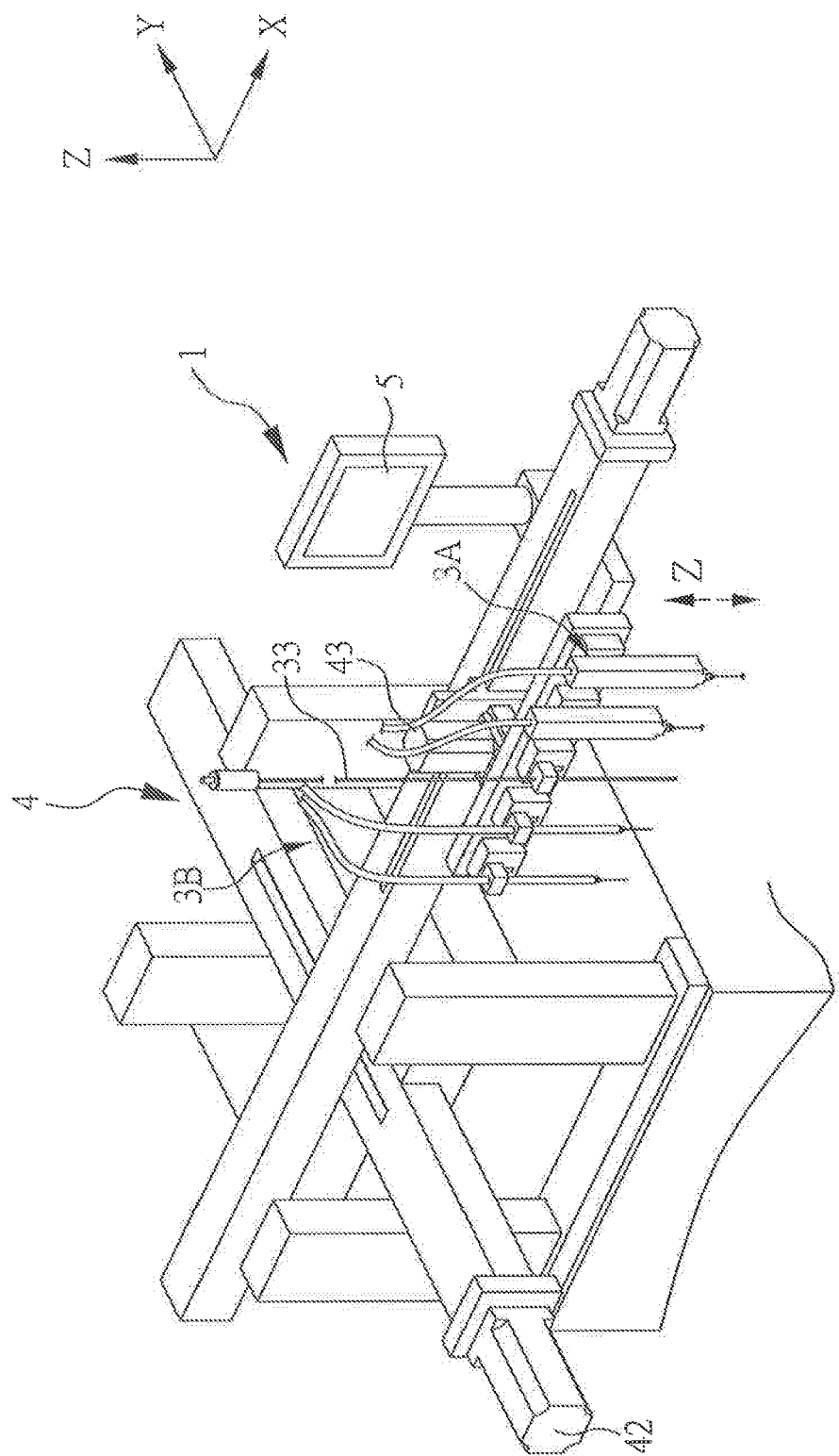
FIG. 4 is a schematic view illustrating the titration units, the electrode unit, and the pipelines of biochip moving alone a Z-axis according to the first embodiment of the present invention.

Now references are made to FIG. 2, a schematic view illustrating titration units, an electrode unit, and pipelines of biochip moving alone an X-axis according to the first embodiment of the present invention; FIG. 3, a schematic view illustrating the titration units, the electrode unit, and the pipelines of biochip moving alone a Y-axis according to the first embodiment of the present invention; and FIG. 4, a schematic view illustrating the titration units, the electrode unit, and the pipelines of biochip moving alone a Z-axis according to the first embodiment of the present invention. According to the present invention, the transfer unit 4 is arranged on the base 2, and includes three driving devices 41, 42, 43 for driving the plural titration units 3A, the electrode unit 33, and the plural pipelines 3B in a lateral direction (leftward and rightward), a longitudinal direction (frontward and rearward) and a vertical direction (upward and downward), respectively. As shown in FIG. 2, the driving device 41 drives the plural titration units 3A, the electrode unit 33, and the plural pipelines 3B moving alone an X-axis; as shown in FIG. 3, the driving device 42 drives the plural titration units 3A, the electrode unit 33, and the plural pipelines 3B moving alone a Y-axis; and as shown in FIG. 4, the driving device 43 drives the plural titration units 3A, the electrode unit 33, and the plural pipelines 3B moving alone a Z-axis. The control unit 5 is electrically connected with the transfer unit 4, and controls the same for switching, selectively, the plural titration units 3A, the electrode unit 33, and the plural pipelines 3B moving alone a direction of X-axis, Y-axis, or Z-axis, respectively. According to the present invention, the driving devices 41, 42, 43 are constituted by servomotors incorporating screws, or incorporating such as rails or sliding blocks, and so forth.

Figure 5A:
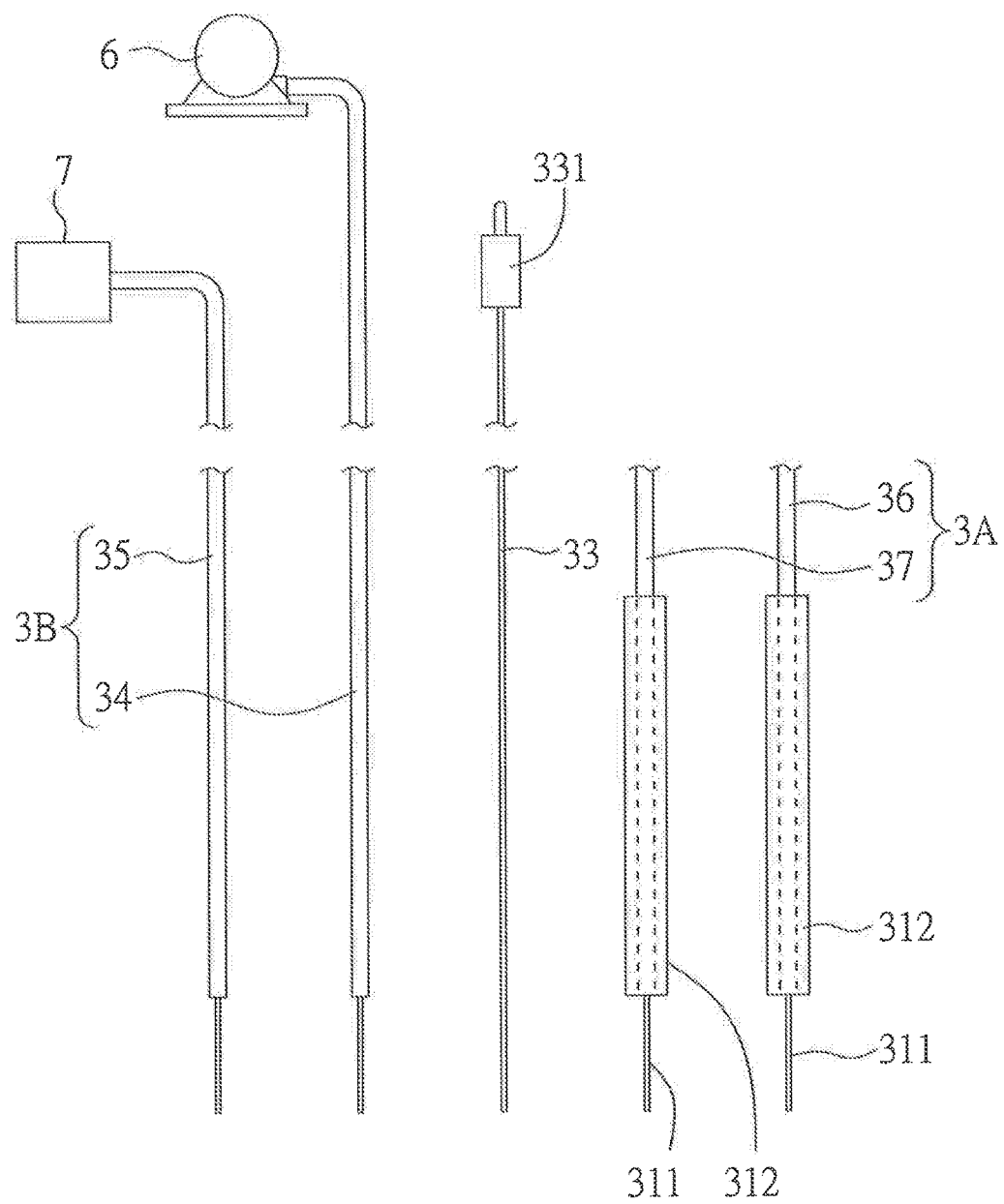
FIG. 5A is a schematic view illustrating the titration units, the electrode unit, and the pipelines of biochip according to the first embodiment of the present invention.

Further referring to FIG. 5A, a schematic view illustrating the titration units, the electrode unit, and the pipelines of biochip according to the first embodiment of the present invention; and also to FIG. 1, the plural titration units 3A refer to two titration units 3A which relate to two titration pipelines 36, 37 for containing different test fluids, respectively. A lower end of each of the titration pipelines 36, 37 is provided with a needle element 311 and a reservoir 312, wherein the reservoirs 312 contain different test fluids. According to the present invention, the transfer unit 4 and the titration pipelines 36, 37 shift their positions so as to drop different test fluids into a to-be-tested biochip 17 (see FIG. 12) such that test speeds can be increased effectively.

According to the present invention, the plural pipelines 3B refer to two pipelines 3B which relate to a vacuum unit 34 and an intake unit 35, wherein the vacuum unit 34 is connected with a vacuum device 6. Thereby, upon finishing inspections, test fluids on the biochip 17 (see FIG. 12) can be removed rapidly, let alone leftover test fluids on the biochip 17 can be reduced. This will increase efficiency and yield rate significantly. Further, the intake unit 35 is connected with an air supply device 7. Thereby, the biochip 17, following removal of the test fluids when the inspection is finished, will be proceeded with an air-blow work. By way of the air blow with compressed air, the leftover test fluids can be blown away and dried instantly. This will prevent the test fluids from flowing to electrode plates of the biochips 17 causing a short circuit or a circuit break. Moreover, electrodes 331 of the electrode unit 33 can provide power supply for dissociating ions from the test fluids so as to perform bioassays.

Figure 5B:
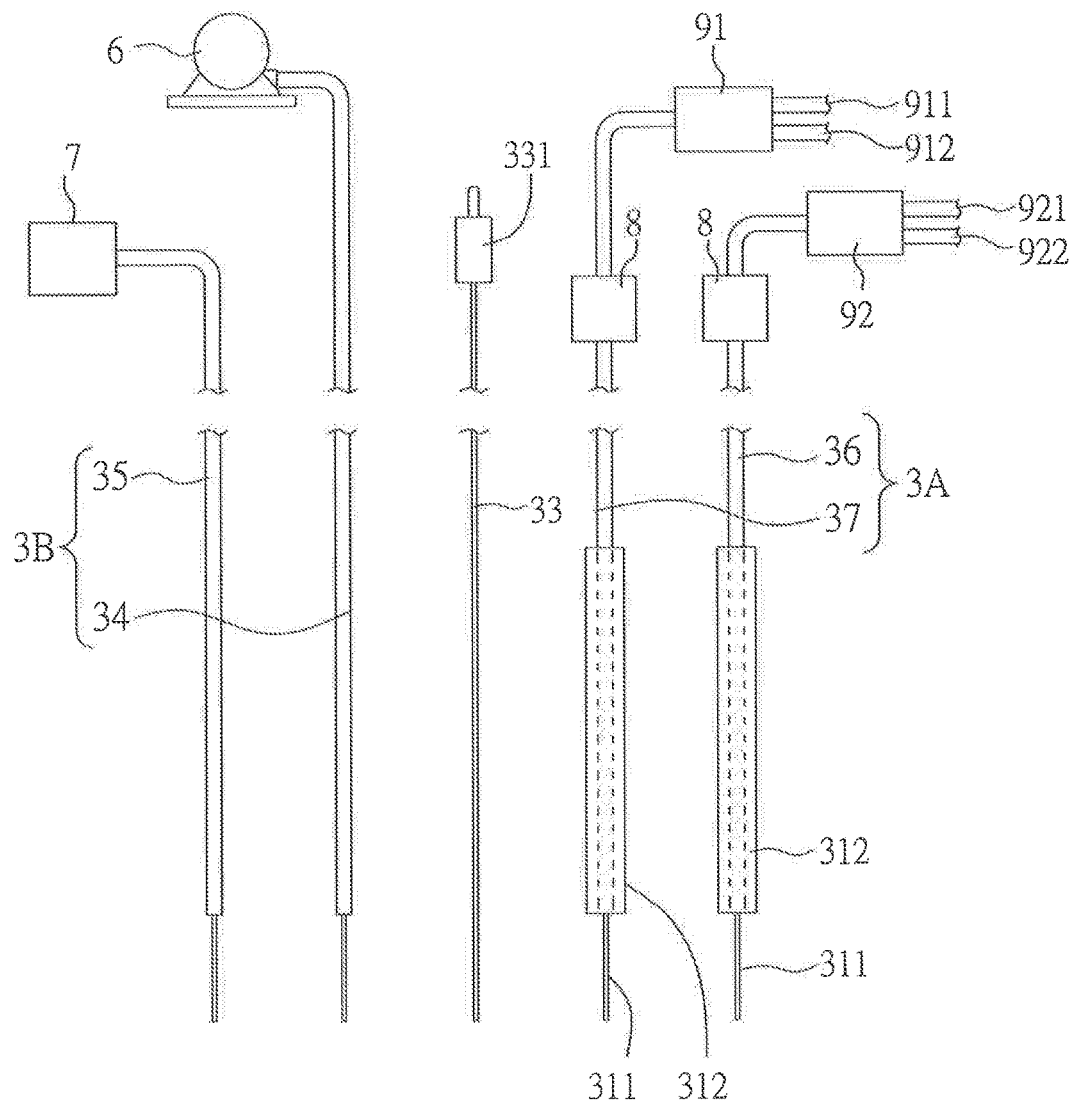
FIG. 5B is a schematic view illustrating titration units, an electrode unit, and pipelines of biochip according to a second embodiment of the present invention.

Further referring to FIG. 5B, a schematic view illustrating titration units, an electrode unit, and pipelines of biochip according to a second embodiment of the present invention, the present embodiment is substantially similar to the first embodiment, except that in the present embodiment, two titration pipelines 36, 37 are each provided with a quantitative fluid control device 8 for controlling titration amount of the test fluids. Besides, the titration pipelines 36, 37 are each provided with a switching device 91, 92, where the switching device 91 is provided for switching two fluid inlet manifolds 911, 912 which contain two different test fluids; whereas the switching device 92 is provided for switching two fluid inlet manifolds 921, 922 which contain two different test fluids. In other words, the four fluid inlet manifolds 911, 912, 921, 922 can contain different test fluids, such that through switching actions of the switching devices 91, 92, interchangeability and convenience of test fluids of various purposes can be enhanced.

Figure 12:
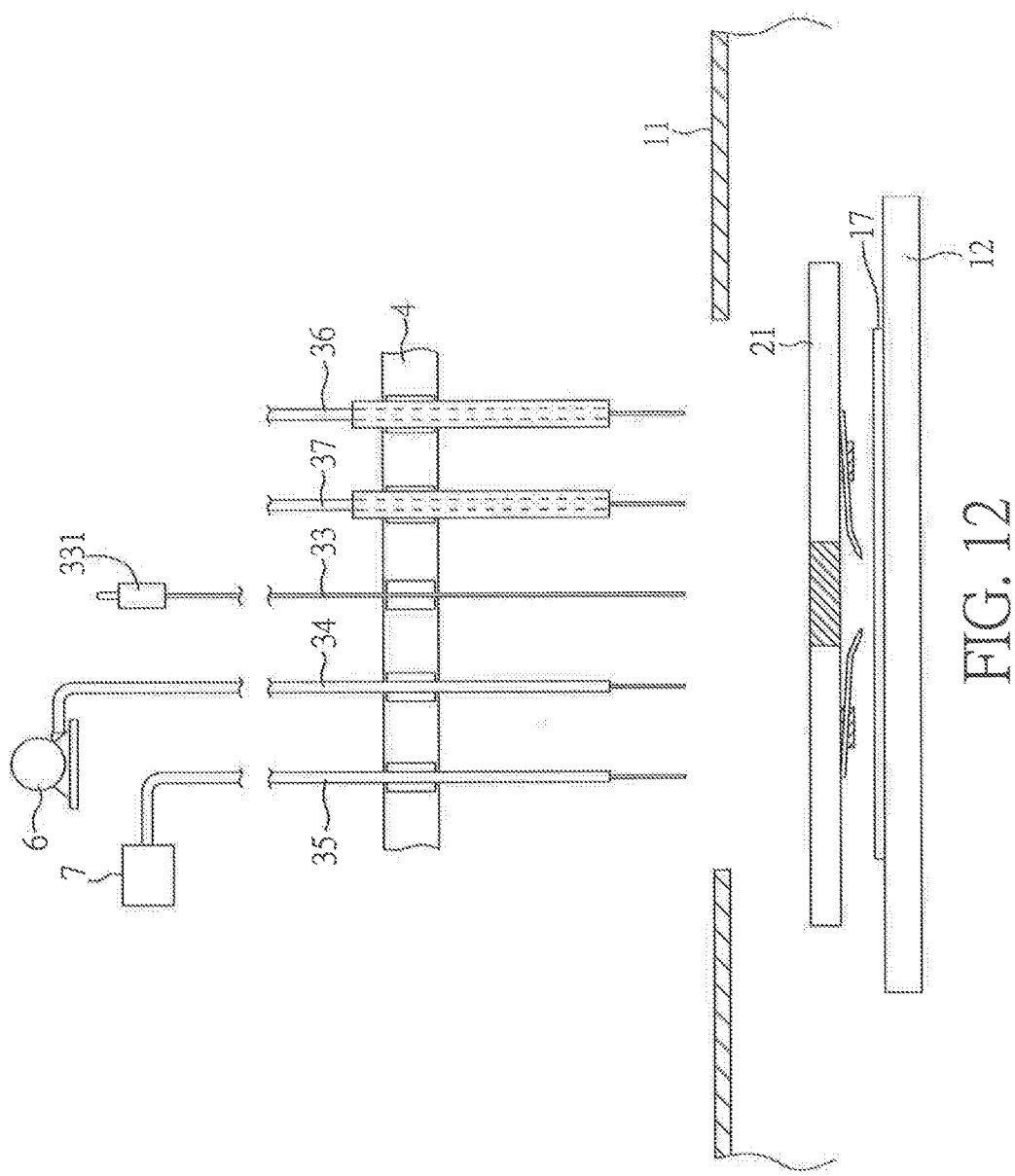
FIG. 12 is a cross-sectional view illustrating part of the titration test apparatus of biochip according to the first embodiment of the present invention.

According to the present invention, examples may be given such that when a test is performed, the control unit 5 can control the transfer unit 4, in accordance with a selected test fluid such as the one contained in the fluid inlet manifold 911, by moving first the titration pipeline 37 to be above the biochip 17 (see FIG. 12). At this moment, the fluid inlet manifolds 911, 912 contain different test fluids. Since the test fluid contained in the fluid inlet manifold 911 is selected, the switching device 91 will open and communicate the titration pipeline 37 and the fluid inlet manifold 911. In the meantime, the fluid inlet manifold 912 will be closed and that the test fluid contained therein will be stopped. The quantitative fluid control device 8 controls the titration amount of the test fluids so as to proceed with the test to the biochip 17.

Similarly, with respect to different test items, suppose the test fluid contained in the fluid inlet manifold 912 is selected, the switching device 91 will open and communicate the titration pipeline 37 and the fluid inlet manifold 912, and in the meantime, the fluid inlet manifold 911 will be closed and that the test fluid contained therein will be stopped. After the test is finished, the transfer unit 4 will move the titration pipeline 37 to another place, and then move the vacuum unit 34 to be above the biochip 17 (see FIG. 12). By using the vacuum device 6 to remove the test fluid speedily, the leftover test fluid can be reduced such that test efficiency and yield rate can be increased significantly. Thereafter, the transfer unit 4 will move the vacuum unit 34 to another place, and then move the intake unit 35 to be above the biochip 17, such than the air blow work is repeated by the air supply device 7. Namely, with the help of compressed air, the leftover test fluid can be blown and dried instantly so as to avoid the test fluid from flowing to the electrode plate of the biochip 17 causing a short circuit or a circuit break. Thereby, in the first and second embodiments, switching actions are performed on the plural titration units 3A, the plural pipeline 3B, and the transfer unit 4 of the titration module 1 so as to drop various test fluids to the biochip 17. This will increase test speed effectively, let alone test efficiency and yield rate will also be improved significantly.

Figures 6, 7:
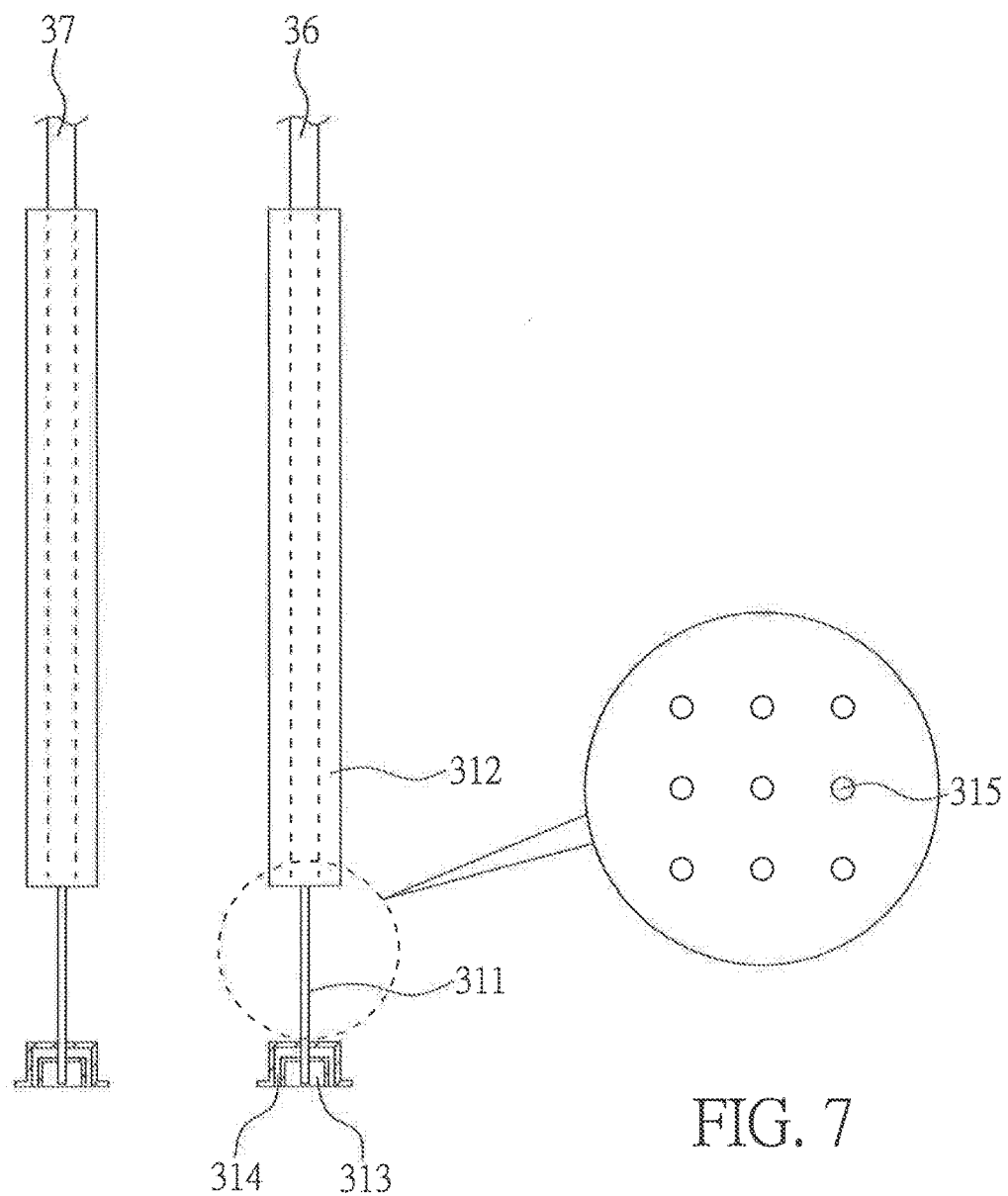
FIG. 6 is a schematic view illustrating titration units of biochip according to a third embodiment of the present invention.
FIG. 7 is a schematic view illustrating titration units of biochip according to a fourth embodiment of the present invention.

Now referring FIG. 6, a schematic view illustrating titration units of biochip according to a third embodiment of the present invention, and also to FIG. 5A, in the present embodiment, a needle element 311 of each titration unit 3A is provided, at its lower end, with a liquid reservoir 313 and a flared flange 314. The flared flange 314 is located at periphery, and extends outward as an extended flange, such that the flared flange 314 can lengthen a "leakage distance" for the test fluids to flow outward. Thereby, in addition to keeping the sufficient test fluid inside the liquid reservoir 313, through the help of the arrangement of the flared flange 314, the "leakage distance" for flowing outward the test fluid is lengthened. This will solve the problem that the test fluid might flow to an ambient circuit board or electrode.

Further referring to FIG. 7, a schematic view illustrating titration units of biochip according to a fourth embodiment of the present invention, and also to FIG. 5A, in the present embodiment, a needle element 311 of each titration unit 3A relates to a micro needle array 315, constituted by a plurality of micro needles in a matrix arrangement, such that the test fluid can be dropped, reliably and uniformly, into a test area of the biochip 17 (see FIG. 12) with the help of the micro needle array 315.

Figure 8:
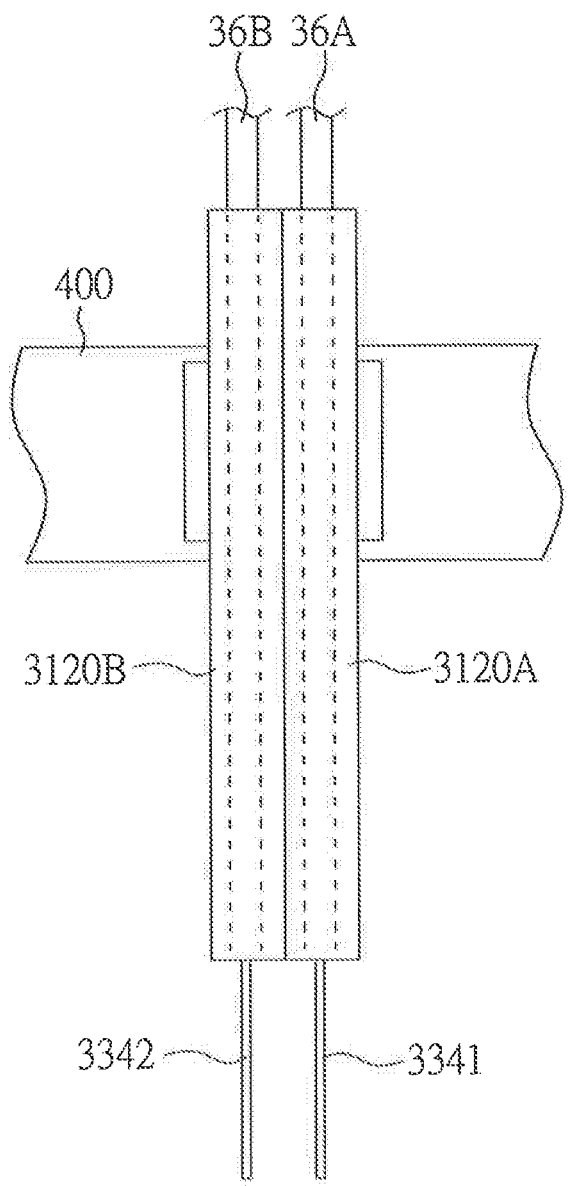
FIG. 8 is a schematic view illustrating titration units of biochip according to a fifth embodiment of the present invention.

Referring to FIG. 8, a schematic view illustrating titration units of biochip according to a fifth embodiment of the present invention, and also to FIG. 5A, in the present embodiment, a titration unit 3A is provided with dual reservoirs 3120A, 3120B of receiving chambers, in connection with titration pipelines 36A, 36B and needle elements 3341, 3342, respectively. The titration unit 3A is conveyed by a driving device 400 such that test fluids of identical constituents can be injected into the dual reservoirs 3120A, 3120B so as to drop the test fluids to multiple specific areas of the biochip 17 simultaneously (see FIG. 12), and to increase the test efficiency. On the other hand, in case the test fluids of different constituents are injected into the dual reservoirs 3120A, 3120B, the driving device 400 will move, in various steps, the titration unit 3A so as to drop the test fluids to the biochip 17. This will prevent the test fluids from cross-contamination, and increase test efficiency.

Figures 9A, 9B:
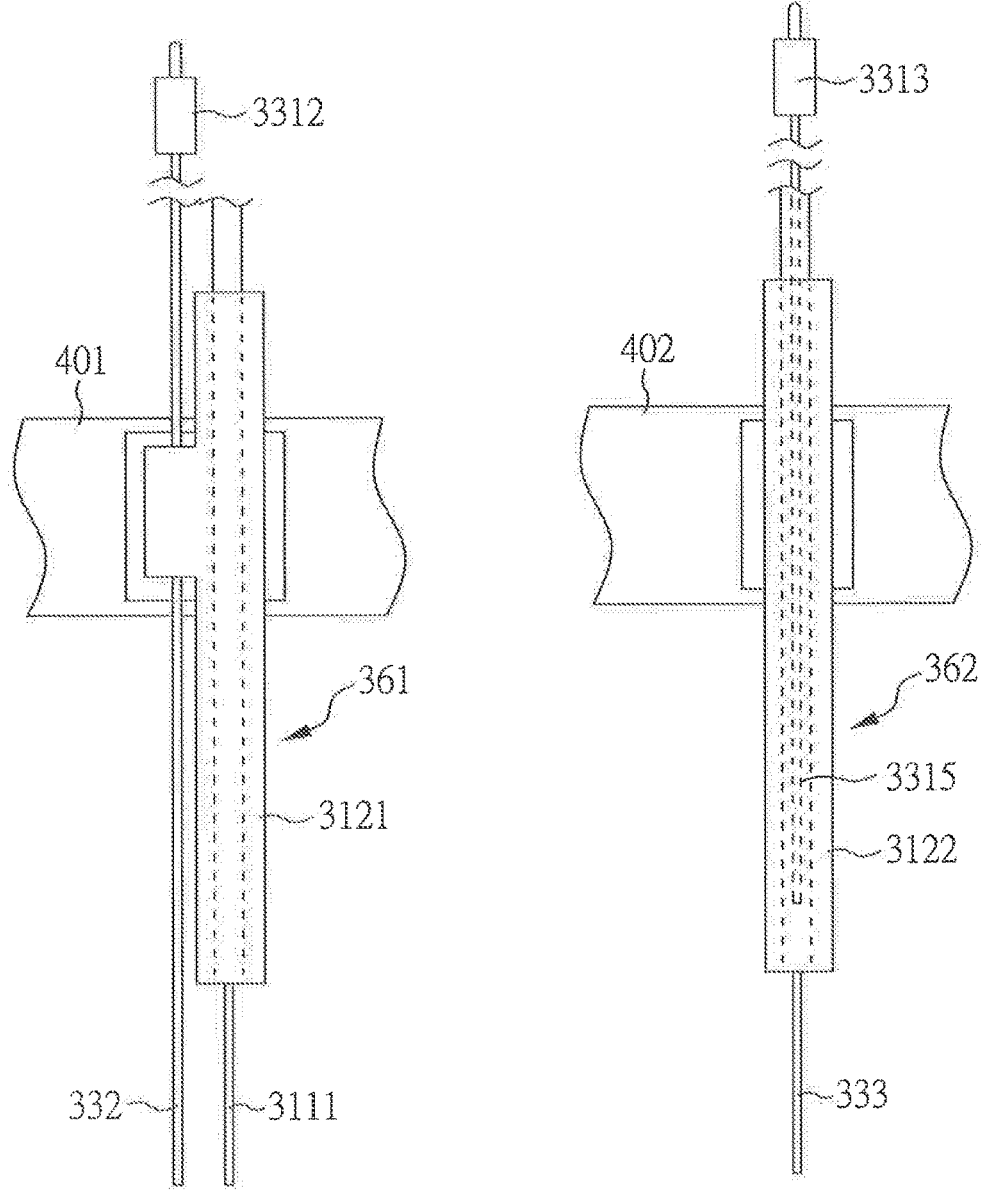
FIG. 9A is a schematic view illustrating titration units and an electrode unit of biochip according to a sixth embodiment of the present invention.
FIG. 9B is a schematic view illustrating titration units and an electrode unit of biochip according to a seventh embodiment of the present invention.

Now referring to FIG. 9A, a schematic view illustrating titration units and an electrode unit of biochip according to a sixth embodiment of the present invention, and also to FIG. 5A, in the present embodiment, a titration pipeline 361 is provided, at its one end, with an electrode 3312, which are then driven and moved, together, by a transfer unit 401. The titration pipeline 361 is provided with a reservoir 3121 and a needle element 3111. Besides, an electrode 3312 has its electrode needle element 332 located at an end of the reservoir 3121, which end is also located for the needle element 3111. Thereby, the transfer unit 401 only requires moving the titration pipeline 361 slightly, a test work for titration of the test fluids and electrolysis of the electrode 3312 can be performed. This will increase inspection speed effectively.

Further referring to FIG. 9B, a schematic view illustrating titration units and an electrode unit of biochip according to a seventh embodiment of the present invention, and also to FIG. 5A, in the present embodiment, a titration pipeline 362 is provided therein an electrode 3313, which are then driven and moved, together, by a transfer unit 402. The titration pipeline 362 includes a reservoir 3122 and a needle element 333, where an electrode needle element 3315, which is electrically connected with the electrode 3313, is inserted in the reservoir 3122, for dissociating ions from the test fluids so as to proceed with the bioassays. In the present embodiment, after dissociation of the test fluids in the reservoir 3122, the biochip 17 is then titrated (see FIG. 12), so that the titration pipeline 362 only requires to move once, through the transfer unit 402, in the X axis and Y axis, and that the work of titration and electrolysis can be carried out simultaneously. This will greatly increase the speed of inspection.

Figures 10A, 10B:
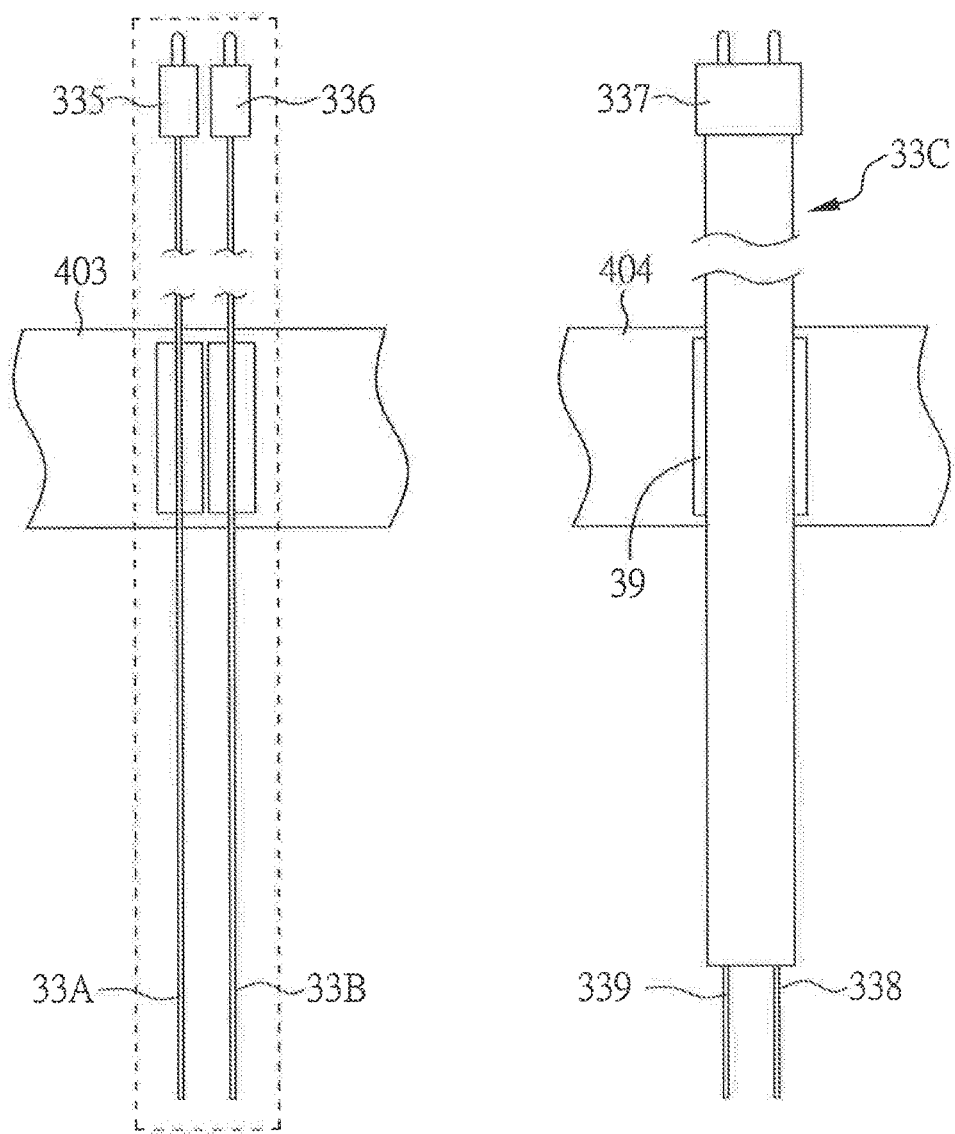
FIG. 10A is a schematic view illustrating an electrode unit of biochip according to an eighth embodiment of the present invention.
FIG. 10B is a schematic view illustrating an electrode unit of biochip according to a ninth embodiment of the present invention.

Referring to FIG. 10A, a schematic view illustrating an electrode unit of biochip according to an eighth embodiment of the present invention; and also FIG. 5A, in the present embodiment, the titration module 1 includes two electrode units 33A, 33B, where the electrode units 33A, 33B are each provided with electrodes 335, 336 for cooperation with the test units, given in the above embodiments, for proceeding with an electrolysis so as to speed up the test work of electrolysis, and to increase the speed of inspection significantly.

Further referring to FIG. 10B, a schematic view illustrating an electrode unit of biochip according to a ninth embodiment of the present invention; and also to FIG. 5, in the present embodiment, the electrode unit 33C includes an electrode 337 and a mounting support 39, where two electrode needle elements 338, 339 are arranged on the mounting support 39. The mounting support 39 is connected with a transfer unit 404 for moving the electrode needle elements 338, 339 together to a corresponding test area of the biochip (see FIG. 12) so as to speed up the test work of electrolysis, and to increase the speed of inspection significantly.

Therefore, it is understood that on the basis of the concept of the present invention, the titration module 1 can rely on a combination structure of the multiple titration units 3A, the electrode unit 33, and the plural pipelines 3B for dropping simultaneously different test fluids on the biochip, and electrolyzing the test fluids. Thus the titration module 1 can increase test speed effectively, and improve test efficiency and yield rate significantly.

Figure 11:
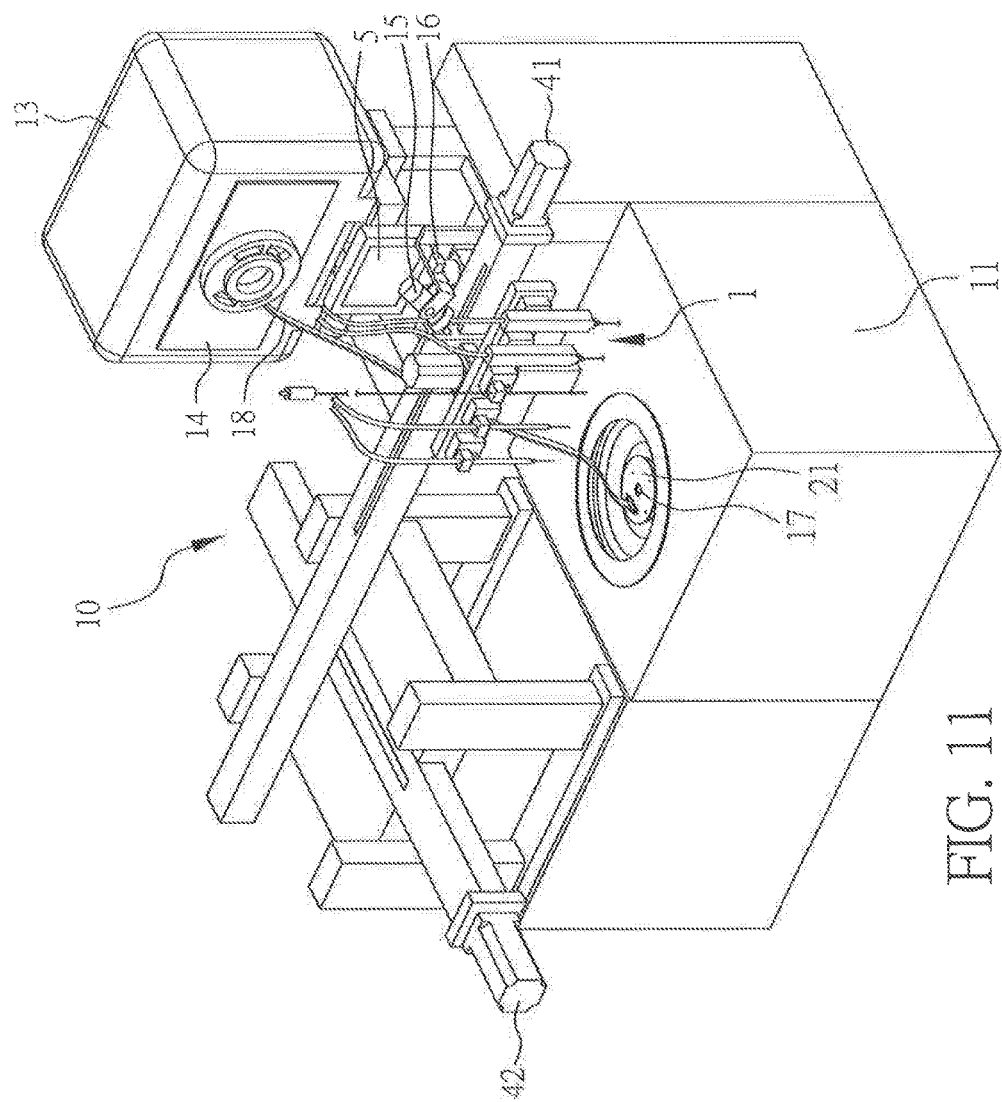
FIG. 11 is a perspective view illustrating a titration test apparatus of biochip according to the first embodiment of the present invention.

Now referring to FIG. 11, a perspective view illustrating a titration test apparatus of biochip according to the first embodiment of the present invention; and to FIG. 12, a cross-sectional view illustrating part of the titration test apparatus of biochip, and also to FIG. 1, the titration test apparatus 10 of biochip comprises a needle test device 11, a titration module 1, a monitor lens 15, a laser rangefinder 16, and a test head 13. The titration test apparatus 10 of biochip is featured in combining the titration module 1 with the needle test device 11 and the test head 13 into an equipment platform. As such, features about the titration module 1 will not be described hereafter, and no further repetition is necessary.

According to the present invention, the titration module 1 is arranged on the needle test device 11, and that the needle test device 11 incorporates the titration module 1, such that the biochip 17, disposed on a mobile stage 12 inside the needle test device 11, can be adjusted to a test position through the mobile stage 12, where the biochip 17 is aligned with the titration module 1 of the needle test device 11 and with a probe card 21 in the needle test device 11 so as to proceed with inspections on test fluids and on electric property. In addition, by connecting a signal line 18 with a test circuit board 14 of the probe card 21 and the test head 13, a real-time transmission and operation to test signals can be performed. As a result, the purpose of fully automatic biochip inspection can be achieved, let alone the efficiency of test can be increased.

Further, according to the present invention, the titration module 1 of the titration test apparatus 10 is provided with the monitor lens 15 and the laser rangefinder 16, such that when a test is performed, the monitor lens 15 and the laser rangefinder 16 can monitor and align with relative positions and relative distances for each of the titration units 3A, of the pipelines 3B, and the electrode unit 33 so as to ensure an accurate alignment.

According to the present invention, the titration test apparatus 10 can integrate effectively the titration module 1 into an automatic titration test apparatus such that test results can be transmitted instantly. This will increase the speed of test effectively and improve test efficiency and yield rate significantly.

Although the present invention has been explained in relation to its preferred embodiments, it is to be understood that many other possible modifications and variations can be made without departing from the scope of the invention as hereinafter claimed.

What is claimed is:

1. A titration test apparatus of biochip, comprising:
   a needle test device, including a mobile stage and a probe card, wherein the mobile stage is provided for carrying a biochip, and the probe card is located above the biochip;

a titration module, including a base, a plurality of titration units, a plurality of pipelines, a transfer unit, and a control unit, wherein the titration units each includes a needle element and a reservoir which are communicated with each other, and the transfer unit is arranged on the base, and is connected with the plural titration units and the plural pipelines, and wherein the transfer unit includes at least one driving device for driving, selectively, the plural titration units and the plural pipelines in a lateral direction (leftward and rightward), a longitudinal direction (frontward and rearward) and a vertical direction (upward and downward), respectively, and the control unit is electrically connected with the transfer unit, and controls the same for switching, selectively, the plural titration units and the plural pipelines; and a test head, provided with a test circuit board which is electrically connected with the probe card.

2. The titration test apparatus of biochip as claimed in claim 1, wherein at least one of the plural pipelines relates to a titration pipeline for connecting with each titration unit.

3. The titration test apparatus of biochip as claimed in claim 2, further comprising a laser rangefinder arranged on the titration module, for detecting distances relative among the titration pipeline, the plural pipelines, and the biochip.

4. The titration test apparatus of biochip as claimed in claim 2, further comprising a monitor lens arranged on the titration module, for detecting distances relative among the titration pipeline, the plural pipelines, and the biochip.

5. The titration test apparatus of biochip as claimed in claim 2, wherein each titration unit is provided, at its lower end, with a liquid reservoir and a flared flange.

6. The titration test apparatus of biochip as claimed in claim 2, wherein each titration unit is provided with a micro needle array.

7. The titration test apparatus of biochip as claimed in claim 2, wherein each titration pipeline is connected, at one side, with an electrode, and each titration pipeline and the electrode are arranged on the transfer unit; and wherein the electrode is electrically connected with an electrode needle element which is located at one side of where the titration pipeline is communicated with the reservoir and the needle element.

8. The titration test apparatus of biochip as claimed in claim 2, wherein each titration pipeline is provided therein with an electrode, and the electrode is electrically connected with an electrode needle element, such that the electrode and the electrode needle element are inserted into the reservoir.

9. The titration test apparatus of biochip as claimed in claim 1, further comprising an electrode unit, which is connected with the transfer unit, for providing power supply for the transfer unit, wherein the at least one driving device of the transfer unit can drive the electrode unit in a lateral direction (leftward and rightward), a longitudinal direction (frontward and rearward) and a vertical direction (upward and downward), respectively.

10. The titration test apparatus of biochip as claimed in claim 1, wherein one of the plural pipelines resides in a vacuum unit for connecting with a vacuum device.

11. The titration test apparatus of biochip as claimed in claim 1, wherein one of the plural pipelines relates to an intake unit which is connected with an air supply device.

* * * * *